US008989843B2

(12) United States Patent
Chien (10) Patent No.: US 8,989,843 B2
(45) Date of Patent: Mar. 24, 2015

(54) METHODS AND APPARATUS FOR ESTIMATING THE POSITION AND ORIENTATION OF AN IMPLANT USING A MOBILE DEVICE

(75) Inventor: Dennis Chien, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 208 days.

(21) Appl. No.: 13/488,827

(22) Filed: Jun. 5, 2012

(65) Prior Publication Data
US 2013/0324839 A1 Dec. 5, 2013

(51) Int. Cl.
*A61B 6/02* (2006.01)
*A61B 6/12* (2006.01)
*G06T 7/00* (2006.01)
*A61B 6/00* (2006.01)
*A61B 19/00* (2006.01)
(Continued)

(52) U.S. Cl.
CPC . *A61B 6/12* (2013.01); *A61B 6/462* (2013.01); *A61B 6/465* (2013.01); *A61B 6/466* (2013.01); *A61B 6/467* (2013.01); *A61B 6/5229* (2013.01); *A61B 2019/5238* (2013.01); *A61B 2019/5287* (2013.01); *A61B 2019/5295* (2013.01); *A61B 2019/5466* (2013.01); *A61F 2/00* (2013.01); *G06F 1/1613* (2013.01); *G06T 7/0046* (2013.01); *G06T 2207/20221* (2013.01); *G06T 2207/30052* (2013.01); *G06T 2207/30204* (2013.01)
USPC ............ 600/424; 600/426; 600/431; 382/131

(58) Field of Classification Search
USPC .................. 600/424, 426, 431; 382/131, 132
See application file for complete search history.

(56) References Cited

U.S. PATENT DOCUMENTS

| 7,801,587 | B2* | 9/2010 | Webber et al. | 600/426 |
|---|---|---|---|---|
| 8,150,494 | B2* | 4/2012 | Simon et al. | 600/414 |
| 2001/0034480 | A1 | 10/2001 | Rasche et al. | |

(Continued)

FOREIGN PATENT DOCUMENTS

WO    2011/148299    12/2011

OTHER PUBLICATIONS

International Search Report dated Sep. 2, 2013, issued in copending PCT application No. PCT/US2013/044263, 12 pgs.
(Continued)

*Primary Examiner* — Baisakhi Roy
(74) *Attorney, Agent, or Firm* — Meunier Carlin & Curfman, LLC (57) ABSTRACT

Methods and apparatus for providing an overlay image of an implant during a surgical procedure using a mobile computing device are provided herein. The implant may include radio-opaque internal markers adjacent to and defining edges of the implant. The method may include: capturing an image of a imaging display device screen; estimating a pose of the implant based on the relationship between the 2-D positions of the radio-opaque internal markers and the 3-D positions of the radio-opaque internal markers; retrieving or generating a 3-D model image of the implant at the determined pose using the 3-D implant data; and overlaying the 3-D model image onto the image of the implant. The captured image may include the implant and at least two of the radio-opaque internal markers being visible as fiducial markers within the image. The fiducial markers may be 2-D positions of the radio-opaque internal markers in a 2-D plane.

20 Claims, 8 Drawing Sheets

(51) Int. Cl.
*A61F 2/00* (2006.01)
*G06F 1/16* (2006.01)

(56) References Cited

U.S. PATENT DOCUMENTS

| | | | |
|---|---|---|---|
| 2006/0285738 A1* | 12/2006 | Boese et al. | 382/131 |
| 2008/0242946 A1 | 10/2008 | Krachman | |
| 2008/0281192 A1* | 11/2008 | Keall et al. | 600/426 |
| 2008/0310698 A1* | 12/2008 | Boeing et al. | 382/131 |
| 2009/0088830 A1 | 4/2009 | Mohamed et al. | |
| 2010/0094308 A1* | 4/2010 | Tatsumi et al. | 606/102 |
| 2011/0110496 A1 | 5/2011 | Foos et al. | |
| 2011/0130651 A1 | 6/2011 | Chen et al. | |
| 2011/0224955 A1* | 9/2011 | Fisker et al. | 703/1 |
| 2011/0262024 A1* | 10/2011 | Bulitta et al. | 382/132 |
| 2011/0282189 A1 | 11/2011 | Graumann | |
| 2013/0131504 A1* | 5/2013 | Daon | 600/424 |
| 2013/0131505 A1* | 5/2013 | Daon et al. | 600/426 |
| 2013/0289390 A1* | 10/2013 | Hermann et al. | 600/424 |
| 2013/0303902 A1* | 11/2013 | Smith et al. | 600/431 |
| 2013/0322726 A1* | 12/2013 | Nathaniel | 382/132 |

OTHER PUBLICATIONS

Anonymous: "What Lies Beneath—An App That Bares It All," Dec. 23, 2011, retrieved from the internet: URL: http://mclodha.wordpress.com/tag/moosejaw/, [retrieved on Oct. 18, 2013], 3 pgs.
DeMenthon et al., Model-Based Object Pose in 25 Lines of Code, Int'l J. Computer Vision (1995).

* cited by examiner

FIG. 7

METHODS AND APPARATUS FOR ESTIMATING THE POSITION AND ORIENTATION OF AN IMPLANT USING A MOBILE DEVICE

BACKGROUND

Polyether ether ketone (PEEK) is a thermoplastic material commonly used in the manufacture of implants. PEEK implants provide many advantages as compared to implants made of metal, such as titanium. For example, PEEK implants have a modulus of elasticity that is more similar to the modulus of elasticity of bone, and therefore, PEEK implants provide for improved biomechanics when implanted into the body. In addition, PEEK, implants are radiolucent (i.e., partly or wholly permeable to radiation). This allows for improved assessment of bony fusion and/or reappearance of cancer.

Because PEEK implants are radiolucent, it is more difficult to intraoperatively determine the exact implant position and orientation. One solution to the problem above is to provide an implant made of a semi-radiolucent PEEK material that is partially visible with a C-arm x-ray system, for example. However, when the PEEK implant is semi-radiolucent, it becomes more difficult to assess bony fusion and/or reappearance of cancer. Another solution to the problem above is to provide radio-opaque internal markers within the PEEK implants that define the edges of the PEEK implants. The markers appear as fiducial markers in the image captured by the C-arm x-ray system and facilitate visual estimation of implant position and orientation. However, even using PEEK implants with radio-opaque markers, it is still difficult to accurately estimate implant position and orientation because the exact distance between the markers and the edges of the implants are not captured in the image.

SUMMARY

A method for providing an overlay image of an implant using a mobile computing device is provided herein. The implant may include radio-opaque internal markers adjacent to and defining edges of the implant. In addition, the mobile computing device may store a library of 3-D implant data including 3-D positions of the internal markers in 3-D space. The method may include: capturing an image of an imaging display device screen; estimating a pose of the implant based on the relationship between the 2-D positions of the radio-opaque internal markers and the 3-D positions of the radio-opaque internal markers; retrieving or generating a 3-D model image of the implant at the determined pose using the 3-D implant data; and overlaying the 3-D model image onto the captured image of the implant. The captured image may include the implant and at least two of the radio-opaque internal markers, which are visible as fiducial markers within the captured image. The fiducial markers may be 2-D positions of the radio-opaque internal markers in a 2-D plane. Further, the 3-D model image may be provided at the estimated pose over the implant.

Optionally, the estimated pose of the implant may be defined by a projection transformation. In addition, the method may further include deriving the projection transformation using the 2-D positions of the internal markers and the 3-D positions of the internal markers.

Alternatively or additionally, the method may include: receiving information related to the implant and/or the surgical procedure; and using the received information when estimating the pose of the implant. The received information may be used to refine the derivation of the projection transformation. In addition, the information may include at least one of an implant family, an implant size, an implant component, an imaging view and a surgical approach.

In another implementation, the method may include requesting information related to the implant and/or the surgical procedure under the condition that the pose of the implant cannot be derived.

In yet another implementation, the method may include performing an image process on the 3-D model image. For example, the image process may include adjusting transparency of the 3-D model image.

One of ordinary skill in the art would understand that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that ail such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. While implementations will be described for estimating the position and orientation of implants using a mobile computing device, it will become evident to those skilled in the art that the implementations are not limited thereto, but are applicable for estimating the position and orientation of any object for which 3-D information is known using a mobile computing device.

Figure 1:
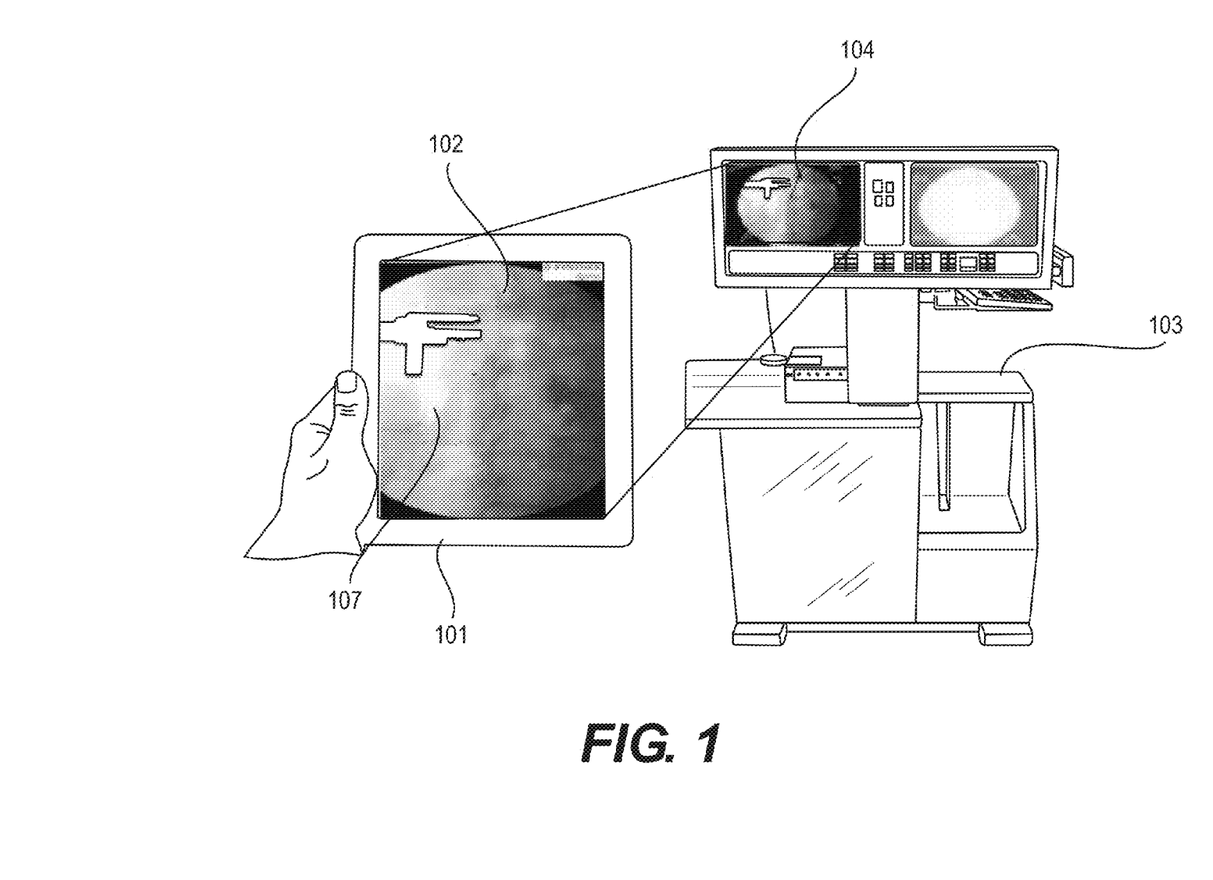
FIG. 1 illustrates a mobile computing device and an imaging device according to an implementation of the invention.

Referring to FIG. 1, a mobile computing device 101 and an imaging device 103 according to an implementation of the invention are shown. The mobile computing device 101 may be used for estimating the position and orientation of implants. The mobile computing device 101 may be implemented as the computing device discussed with regard to FIG. 7, or alternatively as a specialized computing device configured to perform a specific task. For example, in some implementations, the mobile computing device 101 may be an IPAD, available from APPLE, INC., CUPERTINO, Calif. However, in other implementations, the mobile computing device 101 may be another type of portable computing device such as a laptop computer, a tablet, a smart, phone, etc. The imaging device 103 may be a medical imaging device such as a C-arm x-ray system. The imaging device 103 may include an imaging device display screen 104 for displaying an image of a patient such as an x-ray image, for example.

As shown in FIG. 1, the mobile computing device 101 may be capable of capturing an image of the imaging device display screen 104. In order to capture images, the mobile computing device 101 may include an image capturing device (i.e., a digital camera). The captured image 102 may then be displayed by the mobile computing device 101 and optionally stored in memory of the mobile computing device 101. For example, the imaging device 103 may capture, record and/or display an image of an implant inserted within the patient's body during a surgical procedure, which may then be captured and displayed on the mobile computing device 101. The position of the image capturing device of the mobile computing device 101 relative to the imaging device 103 is not critical to the operations discussed below for estimating the position and orientation of the implants. As discussed above, the implant may be made of a PEEK material, which is radiolucent and therefore difficult to identify visually on the imaging device display screen 104 and/or in the captured image 102. For example, a faint outline of the implant 107 may be visible in the captured image 102.

Figure 2:
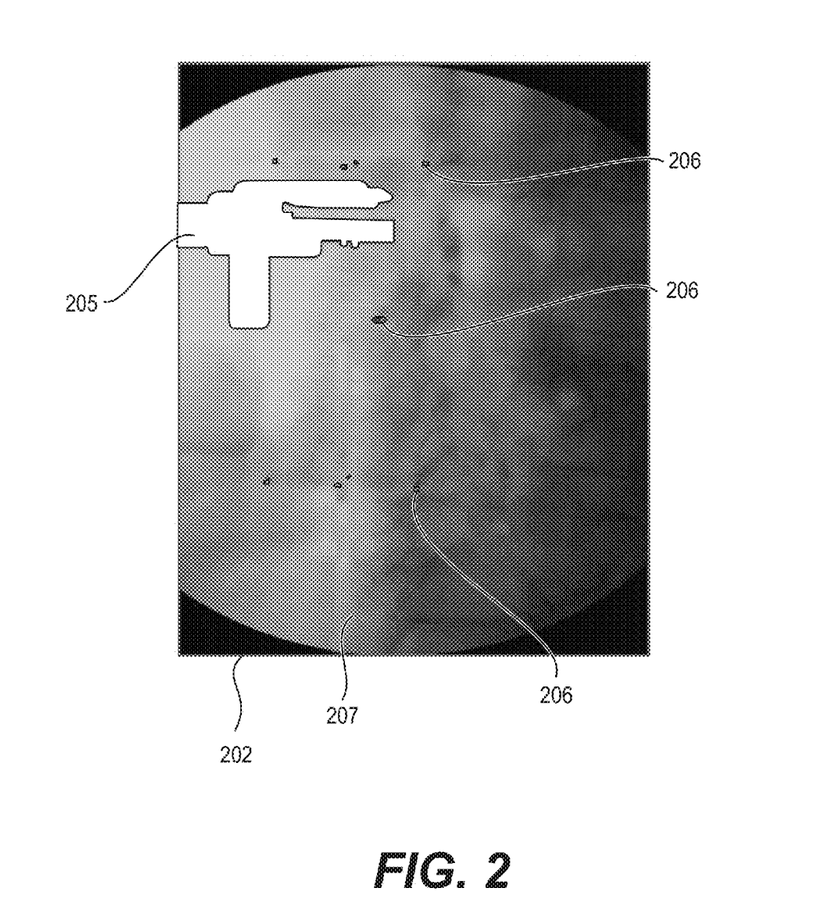
FIG. 2 shows an example captured image of an imaging display device screen showing an A/P view of an implant.

Referring to FIG. 2, an example captured image 202 of an imaging display device screen showing an A/P view of an implant is shown. The captured image 202 may be displayed on the mobile computing device 101 shown in FIG. 1. The captured image 202 may include the implant 207 and a plurality of internal markers 206. In FIG. 2, three fiducial markers 206 are specifically labeled, but additional fiducial markers are visible in the captured image 202. A clamp 205 is also included in the captured image 202. The clamp 205 is a portion of the device that may be utilized during the surgical procedure to position the implant and is visible because it is radio-opaque.

The implant may be formed in a variety of shapes and sizes. For example, the implant may include a ring, a post and endplates fixed to opposite ends of the post (i.e., cranial and caudal endplates). The implant may also be expandable such that the distance between the endplates is adjustable. In addition, the endplates may be various sizes and/or fixed at various angles with respect to the post. As discussed above, if the implant is made of a PEEK material, the implant will be difficult to identify visually within the image (i.e., an x-ray image) because the PEEK material is radiolucent. Thus, in order to assist the surgeon placing the implant, the implant may be provided with radio-opaque internal markers. The radio-opaque internal markers are placed adjacent to and define the edges of the implant. For example, the radio-opaque internal markers may be placed 1 mm from the edges of the implant. The implant may be designed such that the radio-opaque internal markers assist the surgeon in visualizing the structural features of the implant. In fact, the radio-opaque internal markers allow the surgeon to visualize an implant having any shape, size and/or feature. Accordingly, the radio-opaque internal markers allow the surgeon to estimate the position and orientation (i.e., a pose of the implant) of the implant during surgery. However, even when a well-designed implant includes radio-opaque internal markers, it may still be difficult for the surgeon to estimate the position and orientation of the implant during surgery because it is not possible to visually identify the edges of the implant.

The pose of an object (i.e., the implant) is defined as the position and orientation of the object relative to a coordinate system such as, but not limited to, a Cartesian coordinate system in three-dimensional (3-D) space. One of ordinary skill in the art would understand that there are many algorithms for estimating the pose of an object relative to 3-D space using a two-dimensional (2-D) image of the object. In particular, the pose of an object can be estimated based on an approximate 3-D model of the object and a 2-D image of the object. The 2-D image of the object may preferably include a number of points (i.e., 2-D to 3-D correspondences) of the approximate 3-D model of the object. Different algorithms may require different numbers of 2-D to 3-D correspondences in order to estimate the pose of the object. In addition, the position of the image capturing device at the time of capturing the 2-D image is not critical to estimating the pose of the object.

As discussed above, the implant may include a number of radio-opaque internal markers that are adjacent to and define edges of the implant. The positions of the radio-opaque markers in 3-D space are fixed. The positions of the radio-opaque 3-D markers may be included in the 3-D implant data, which may be stored in memory of the mobile computing device 101 shown in FIG. 1. Because the internal markers are radio-opaque, the internal markers may be visible as fiducial markers within an image of the implant such as an image captured by a C-arm x-ray system, for example. For example, the radio-opaque internal markers of the implant may be visible as the fiducial markers 206 shown in the captured image 202 of FIG. 2. The fiducial markers are 2-D positions of the radio-opaque internal markers in a 2-D image plane (i.e., the captured image). It is possible to map the 3-D positions of the radio-opaque internal markers of the implant onto the 2-D image plane using a transformation. The transformation may be any function that maps one set of points to another set of points. For example, the transformation may be the function that maps each point in 3-D space (i.e., a radio-opaque internal marker) to its corresponding point (i.e., a fiducial marker) in the 2-D image plane. Example transformations include, but are not limited to, perspective and orthographic projections. The transformation may be used to define the pose of the object. Accordingly, the pose of the implant (or the transformation) may be derived based on the relationships, or correspondences, between the 3-D positions of the radio-opaque internal markers in 3-D space and the 2-D positions of the fiducial markers in the 2-D image plane.

One example algorithm is the POSIT algorithm, which is capable of estimating the pose (i.e., 3-D rotation and translation) of the implant based only on a single 2-D image of the implant. The POSIT algorithm requires an approximate 3-D model of the implant (i.e., 3-D implant data including 3-D positions of the radio-opaque internal markers in 3-D space) and 2-D to 3-D correspondences. The POSIT algorithm may require correspondences between at least four non-coplanar 2-D and 3-D points in order to estimate the pose of the implant with sufficient accuracy. The POSIT algorithm first approximates the perspective projection using a scaled orthographic projection and finds the rotation matrix and translation vector. The POSIT algorithm then iteratively calculates scaled orthographic projections at each 2-D to 3-D correspondence and approximates the perspective projection using the iteratively corrected projections. The POSIT algorithm is discussed in detail in DeMenthon et al, Model-Based Object Pose in 25 Lines of Code, *International Journal of Computer Vision* 15:123-41 (1995). One of ordinary skill in the art would understand that the POSIT algorithm is only one example algorithm and that additional algorithms for estimating the pose of an object are available.

Figure 3:
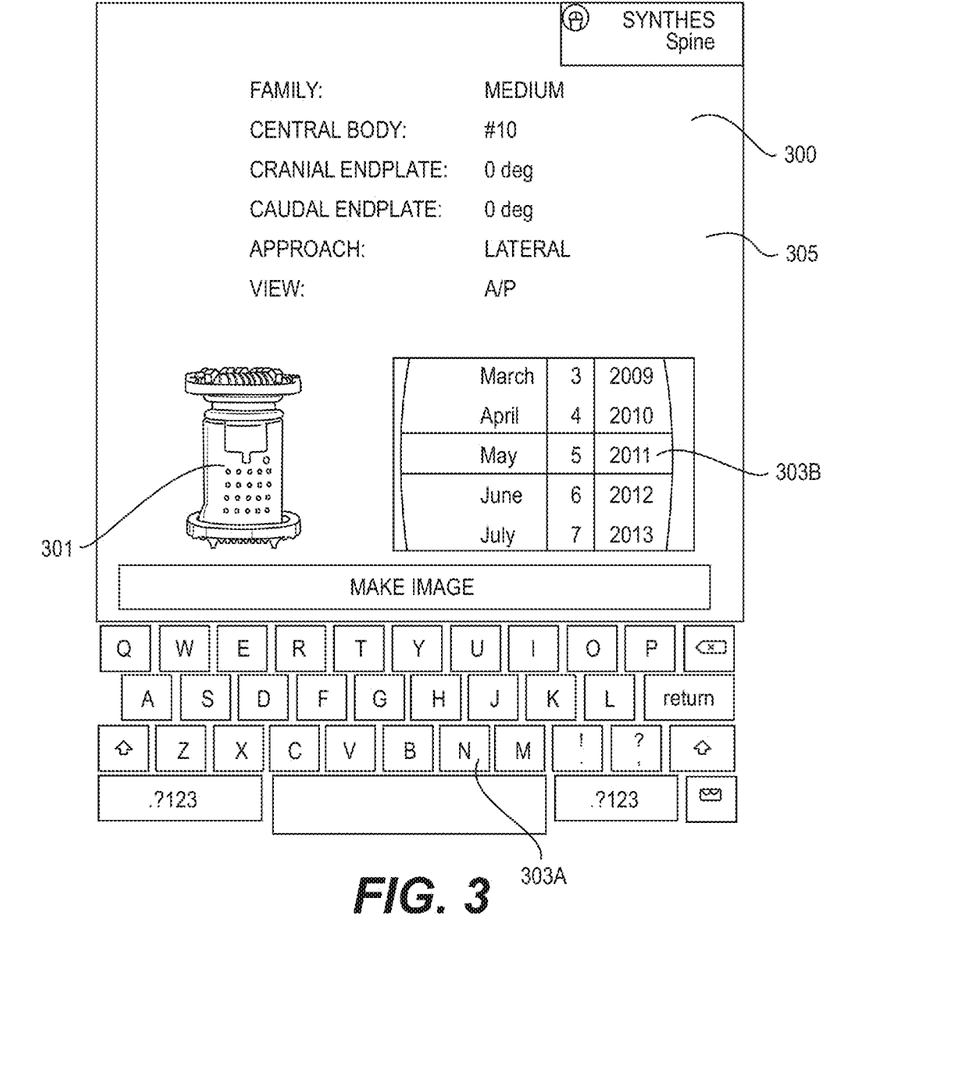
FIG. 3 shows an example information input display screen for display on the mobile computing device.

Referring to FIG. 3, an example information input display screen 300 of the mobile computing device is shown. Optionally, additional information regarding the implant and/or the surgical procedure may be obtained. This additional information may be used to refine the estimated pose of the implant. For example, as shown in FIG. 3, the additional information, such as, but not limited to a family type of the implant and an approach of a surgical procedure may allow certain positions and orientations to be ruled out. Alternatively or additionally, the additional information may be requested in the event that the pose of the implant cannot be calculated based on the 2-D to 3-D correspondences. In some implementations, the additional information may be needed to estimate the pose of the implant. In particular, there may be cases where too many radio-opaque internal markers are obscured such that some of the radio-opaque internal markers are not visible as fiducial markers in the captured image, which may result in too few 2-D to 3-D correspondences. Having too few 2-D to 3-D correspondences may lead to an inaccurate estimated pose of the implant. However, by providing additional information regarding the implant and/or the surgical procedure in addition to the 2-D to 3-D correspondences, it may be possible to estimate the pose of the implant.

As shown in FIG. 3, the information input display screen 300 may be displayed on the mobile computing device 101 shown in FIG. 1. The information input display screen 300 may provide a mechanism 305 for entering additional information regarding the implant and/or the surgical procedure and an input section 303A and 303B. The mechanism 305 may include entry fields corresponding to categories of requested information. The categories of requested information may include, but are not limited to the implant family, the size of the central body, information regarding the endplates, the surgical approach and the image view (i.e., the medical imaging device image view). As discussed above, the implant may be formed in a variety of shapes and sizes. Accordingly, different implants may be grouped into different implant families based on structural differences (i.e., posts, rings, endplates, etc.) and/or sizes of the various implants. In addition, different implants may be formed from various structural components having different sizes and/or orientations. In FIG. 3, for example, the size of the central body is indicated as #10 and the orientations of the cranial and caudal endplates relative to the central body are indicated as 0 degrees. The additional information regarding the implant shown in FIG. 3 provides information regarding the position and orientation of the implant, which may be used in refining the estimated the pose of the implant based on the 2-D to 3-D correspondences. Further, additional information regarding the surgical procedure such as the surgical approach (i.e., lateral) and/or the image view (i.e., A/P or lateral) provides information regarding the position and orientation of the implant. Similarly to the additional information regarding the implant, the additional information regarding the surgical procedure may be used in refining the estimated the pose of the implant based on the 2-D to 3-D correspondences.

The information input display screen 300 may also provide an input section 303A and 303B. In FIG. 3, the input section is a touch screen including the keyboard input section 303A and a scrolling input section 303B. The input section 303A and 303B may allow the user to enter the additional information regarding the implant and/or the surgical procedure. Although the input section shown is a touch screen, it may be possible to implement the input section in another manner such as using input keys, buttons, knobs, etc. provided on the mobile computing device 101 shown in FIG. 1.

Figure 4A:
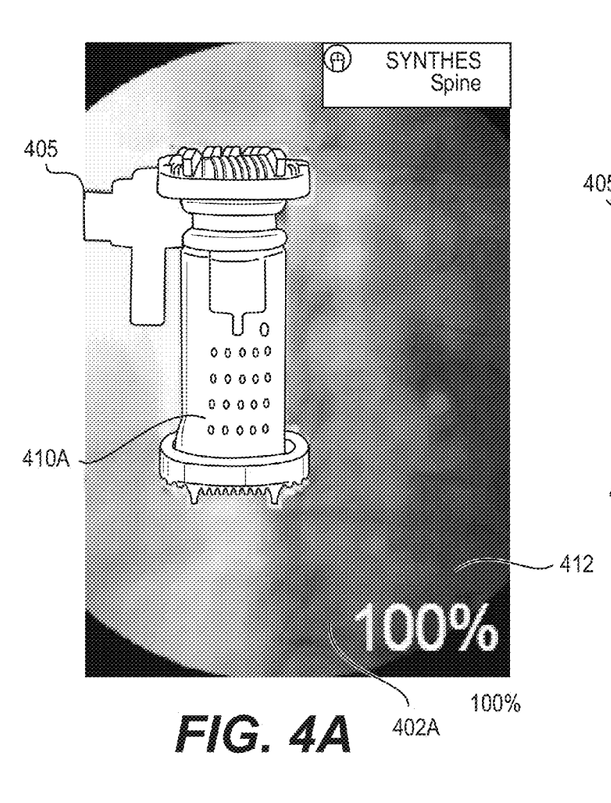
FIGS. 4A and 4B show example captured images of an imaging display device screen showing an A/P view of an implant along with a 3-D model image of the implant.
Figure 4B:
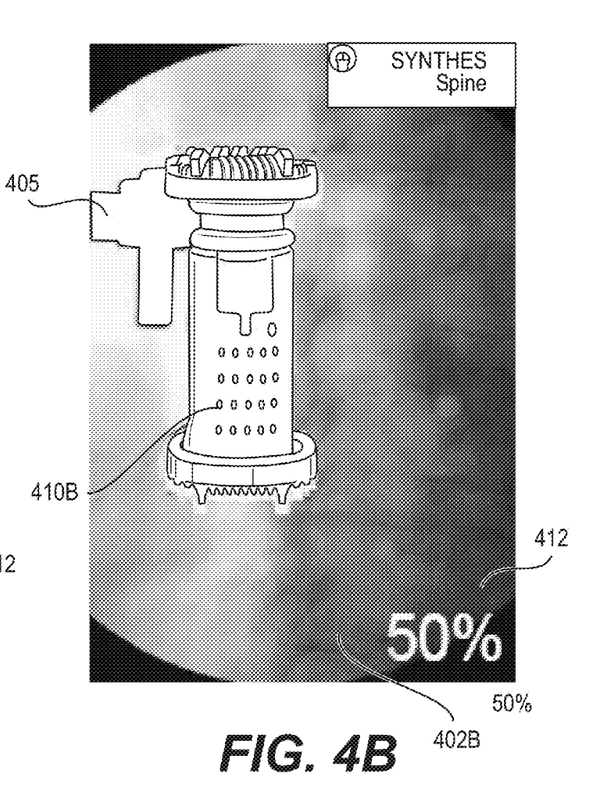

FIGS. 4A and 4B show example captured images 402A and 402B of an imaging display device screen showing an A/P view of an implant along with a 3-D model image. The captured images 402A and 402B may be displayed on the mobile computing device 101 shown in FIG. 1. The captured images 402A and 402B may include a 3-D model image 410A and 410B, a clamp 405, a relative transparency amount 412, as well as any other information such as marketing material, for example. The captured images 402A and 402B differ from the captured image 202 shown in FIG. 2 in that the 3-D model images 410A and 410B are provided as overlays on the captured image 402A and 402B. As discussed above, it may be possible to estimate the pose of the implant based on the 2-D to 3-D correspondences. In other words, it may be possible to estimate the pose of the implant based on the relationship between the 3-D positions of the radio-opaque internal markers in 3-D space and the corresponding 2-D positions of the fiducial markers in the captured image. Alternatively or additionally, information regarding the implant and/or the surgical procedure may also be utilized to refine the estimated pose of the implant based on the 2-D to 3-D correspondences. After estimating the pose of the implant (i.e., deriving the projection transformation based on the 2-D to 3-D correspondences), a 3-D model image 410A and 410B may be retrieved from a database of images, which may be included in the 3-D implant data. Alternatively or additionally, the 3-D model image 410A and 410B may be generated. For example, the 3-D model image 410A and 410B may be generated using 3-D implant data including, but not limited to, the 3-D positions of the radio-opaque internal markers and color, texture, and/or surface features of the implant. The 3-D implant data may be stored in memory of the mobile computing device 101 shown in FIG. 1. The 3-D model image 410A and 410B may then be provided as an overlay on the captured image 402A and 402B. The 3-D model image 410A and 410B may be provided in the same position and at the same orientation as the implant within the patient's body, which allows the surgeon to visualize the position and orientation of the implant.

After generating the 3-D model image 410A and 410B, it may be possible to perform image processing on the generated 3-D model image 410A and 410B. One example image process to perform on the generated 3-D model image 410A and 410B is adjusting the transparency. For example, it may be possible to increase and/or decrease the transparency of the 3-D model image 410A and 410B. By increasing and/or decreasing the transparency, the 3-D model image 410A and 410B becomes more or less visible as compared to the captured image 402. The 3-D model image 410B shown in FIG. 413 is shown as more transparent (i.e., 50%) than the 3-D model image 410A shown in FIG. 4A (i.e., 100%). The relative amount of transparency 412 may also be provided over the captured image 402.

Figure 5A:
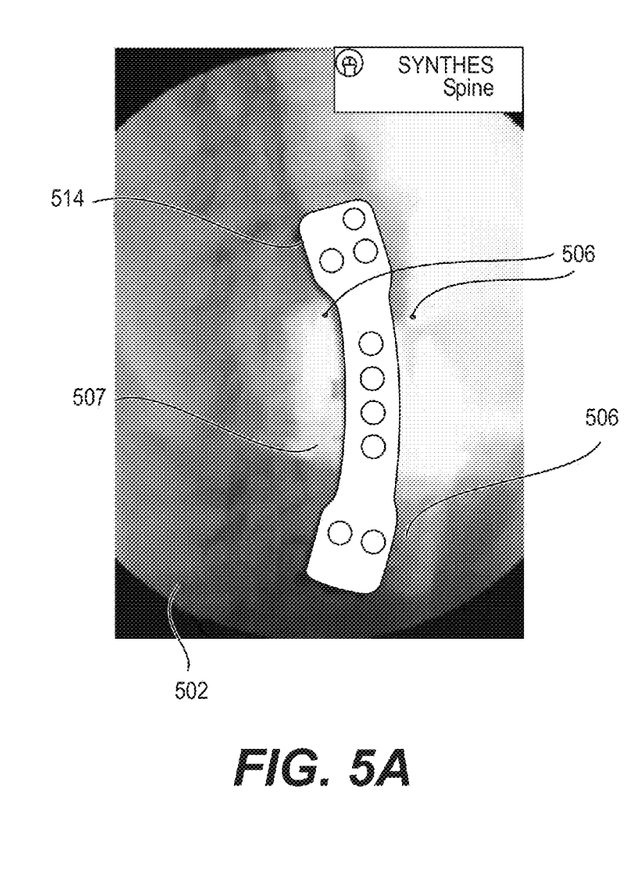
FIG. 5A shows an example captured image of an imaging display device screen showing a lateral view of an implant.
Figure 5B:
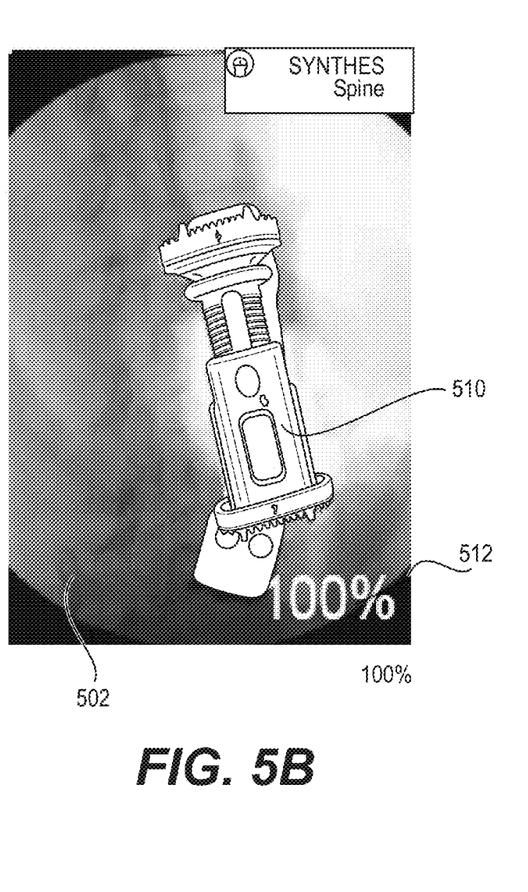
FIG. 5B shows an example captured image of an imaging display device screen showing a lateral view of implant along with a 3-D model image of the implant.

FIG. 5A shows an example captured image 502 of an imaging display device screen showing a lateral view of an implant. The perspective view of the captured image 502 (i.e., lateral view) shown in FIG. 5A differs from the perspective view of the captured image 202 (i.e., A/P view) shown in FIG. 2. The captured image 502 therefore includes the implant 507, fiducial markers 506 and a plate 514 (i.e., a portion of the device used to position the implant during the surgical procedure). The implant 507, fiducial markers 506 and plate 514 are captured from a different image view (i.e., lateral versus A/P), and therefore, the perspective has changed between images. Similarly to above, it is possible to estimate the pose of the implant and then generate a 3-D model image of the implant, which can be provided as an overlay over the captured image. This is shown in FIG. 5B where the 3-D model image 510 is provided as an overlay over the captured image 502. In addition, it may be possible to perform an image process on the 3-D model image such as adjusting the transparency. The relative amount of transparency 512 may also be provided over the captured image 502.

Figure 6A:
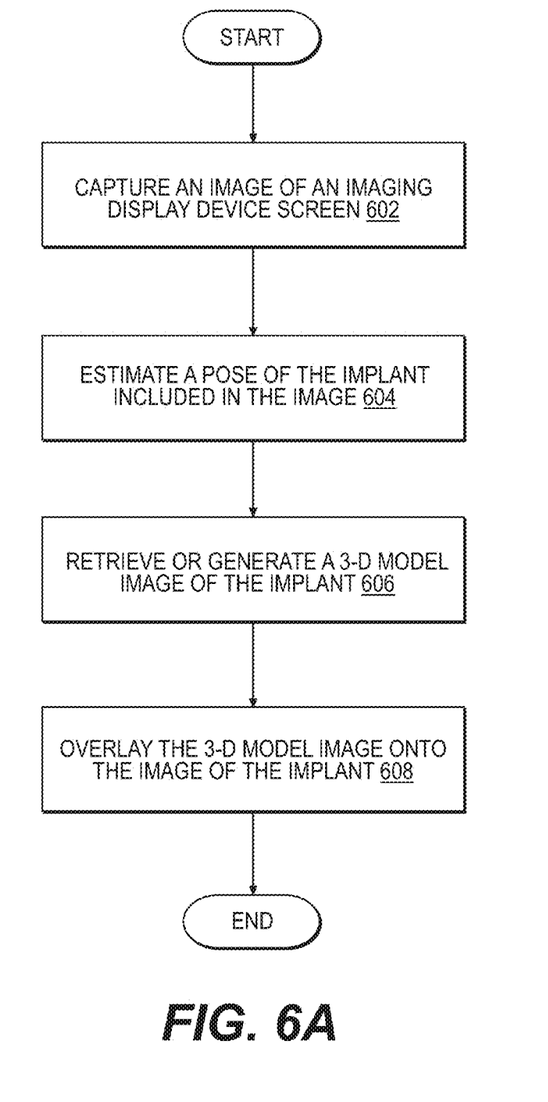
FIGS. 6A and 6B illustrates example operations for providing an overlay image of an implant during a surgical procedure using a mobile computing device.

Referring to FIG. 6A, example operations for providing an overlay image of an implant during a surgical procedure using a mobile computing device are shown. At 602, an image of an imaging display device screen may be captured. For example, an imaging device 103 such as a C-arm x-ray system shown in FIG. 1 may include an imaging device display screen 104 on which an image may be displayed. It may be possible to capture an image of the imaging device display screen 104 using the mobile computing device 101 shown in FIG. 1. The position of the image capturing device of the mobile computing device is not critical to estimating the pose of the implant. After capturing an image of the imaging display device screen, it may be possible to estimate a pose (i.e., the position and orientation of the implant) included in the captured image. For example, the pose of the implant may be estimated based on an approximate 3-D model of the implant and a 2-D image of the implant. The approximate 3-D model of the implant may be stored as 3-D implant data in memory of the mobile computing device, for example. The 3-D implant data may preferably include the 3-D positions of the radio-opaque internal markers in 3-D space. In addition, the radio-opaque internal markers may be visible as fiducial markers in the 2-D image. Accordingly, it may be possible to derive the projection transformation based on correspondences between the 3-D positions of the radio-opaque internal markers and the 2-D positions of the fiducial markers. As discussed above, one of ordinary skill in the art would understand that there are many algorithms available for estimating the pose of the implant based on the 2-D to 3-D correspondences. After estimating a pose of the implant, it may be possible to retrieve a 3-D model image from a database of images or generate a 3-D model image of the implant using the 3-D implant data at 606, for example. The 3-D model image of the implant may be a 3-D representation of the implant at the estimated pose. At 608, the 3-D model image may be provided as an overlay on the captured image. The 3-D model image may be provided in the same position and at the same orientation as the implant within the patient's body, which allows the surgeon to visualize the position and orientation of the implant.

Figure 6B:
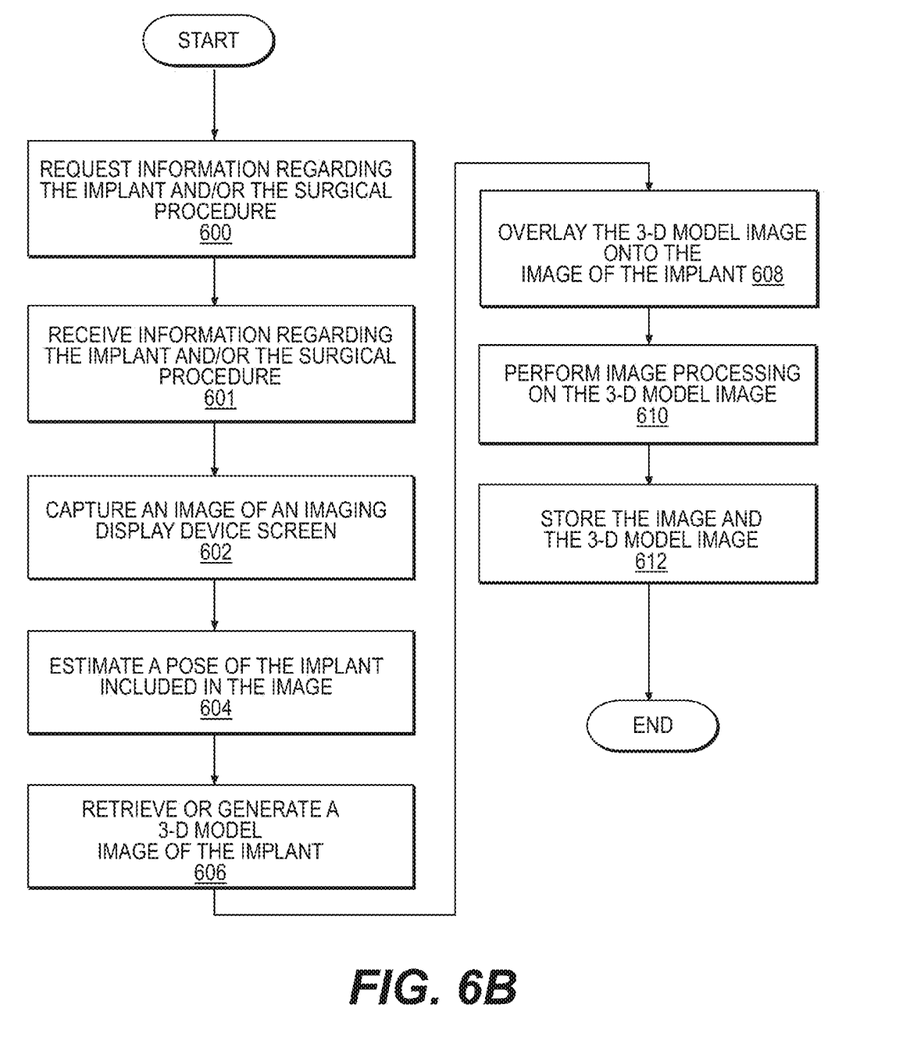

Referring to FIG. 6B, example operations for providing an overlay image of an implant during a surgical procedure using a mobile computing device are shown. Many of the operations shown in FIG. 6B are similar to the operations shown in FIG. 6A and are therefore not discussed in detail below. At 600, it may be possible to request information regarding the implant and/or the surgical procedure. The requested information may include, but is not limited to, the implant family, the size of the implant, the implant components, the surgical approach and the image view. The requested information may be used to refine the estimated pose of the implant based on the 2-D to 3-D correspondences. For example, as discussed above, the additional information may be requested in the event that the pose of the implant cannot be calculated based on the 2-D to 3-D correspondences such as in the case where too many radio-opaque internal markers are obstructed and not visible as fiducial markers in the captured image. This may result in too few 2-D to 3-D correspondences to accurately estimate the pose of the implant. At 601, it may be possible to receive information regarding the implant and/or the surgical procedure. As shown in FIG. 3, the information may be requested and received using an information input display screen displayed on the mobile computing device.

At 610, after estimating the pose of the implant and generating a 3-D model image of the implant, an image process may be performed on the 3-D model image of the implant. For example, it may be possible to adjust the relative transparency of the 3-D model image. By adjusting the relative transparency of the 3-D model image, the 3-D model image may become more or less visible as compared to the captured image. Adjusting the transparency of the 3-D model image is only one example of an image process that may be performed on the 3-D model image, and one of ordinary skill in the art would understand that additional image processes may be performed. It may also be possible to store the image of the implant along with the 3-D model image at 612. For example, the captured image including the 3-D model image overlay may be stored in memory of the mobile computing device. By storing the captured image including the 3-D model image overlay, it may be possible to share the captured image. For example, the captured image including the 3-D model image overlay may be e-mailed to a remote consultant, stored in electronic medical record, etc.

Figure 7:
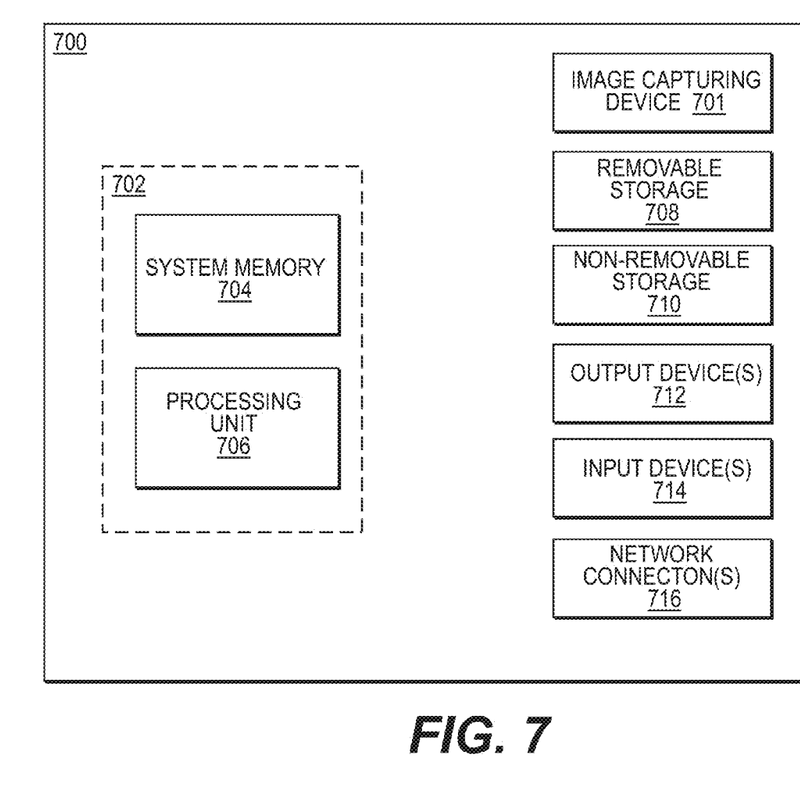
FIG. 7 is a block diagram illustrating an example computing device.

Referring to FIG. 7, a block diagram of an example computing device is illustrated. The mobile computing device discussed above may be a computing device, such as computing device 700 shown in FIG. 7. In its most basic configuration, computing device 700 typically includes at least one processing unit 706 and memory 704. Depending on the exact configuration and type of computing device, memory 704 may be volatile (such as random access memory (RAM)), non-volatile (such as read-only memory (ROM)), flash memory, etc.), or some combination of the two. This most basic configuration is illustrated in FIG. 7 by dashed line 702. The processing unit may be a standard programmable processor that performs arithmetic and logic operations necessary for operation of the computing device 700. The computing device may also include an image capturing device 701, such as a digital camera. The image capturing device 701 may be capable of capturing images that may be stored in memory of the computing device 700.

The processing unit 706 may be configured to execute program code encoded in tangible, computer-readable media. For example, the processing unit 706 may execute program code stored in the system memory 704.

Computing device 700 may have additional features/functionality. For example, computing device 700 may include additional storage such as removable storage 708 and non-removable storage 710 including, but not limited to, magnetic or optical disks or tapes. Computing device 700 may also contain network connection(s) 716 that allow the device to communicate with other devices. Computing device 700 may also have input device(s) 714 such as a keyboard, mouse, touch screen, etc. Output device(s) 714 such as a display, speakers, printer, etc. may also be included. All these devices are well known in the art and need not be discussed at length here.

Computing device 700 typically includes a variety of computer readable media. Computer readable media can be any available media that can be accessed by device 700 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 704, removable storage 708, and non-removable storage 710 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 700. Any such computer storage media may be part of computing device 700.

It should be understood that the various techniques described herein may be implemented in connection with hardware, firmware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for providing an overlay image of an implant using a mobile computing device, the implant including radio-opaque internal markers adjacent to and defining edges of the implant, the mobile computing device storing a library of 3-D implant data including 3-D positions of the radio-opaque internal markers in 3-D space, the method comprising:
    capturing an image of an imaging display device screen, the image including the implant and at least two of the radio-opaque internal markers being visible as fiducial markers within the captured image, the fiducial markers being 2-D positions of the radio-opaque internal markers in a 2-D plane;
    estimating a pose of the implant based on the relationship between the 2-D positions of the radio-opaque internal markers and the 3-D positions of the radio-opaque internal markers;
    retrieving or generating a 3-D model image of the implant at the determined pose using the 3-D implant data; and
    overlaying the 3-D model image onto the captured image, wherein the 3-D model image is provided at the estimated pose over the implant.

2. The method of claim 1, wherein the estimated pose of the implant is defined by a projection transformation, and estimating a pose of the implant further comprises deriving the projection transformation using the 2-D positions of the radio-opaque internal markers and the 3-D positions of the radio-opaque internal markers.

3. The method of claim 2, further comprising:
    receiving information related to the implant and/or the surgical procedure; and
    using the received information when estimating the pose of the implant, wherein the received information is used to refine the derivation of the projection transformation.

4. The method of claim 3, wherein the information comprises at least one of an implant family, an implant size, an implant component, an imaging view and a surgical approach.

5. The method of claim 3, further comprising requesting information related to the implant and/or the surgical procedure under the condition that the pose of the implant cannot be derived.

6. The method of claim 1, further comprising performing an image process on the 3-D model image.

7. The method of claim 6, wherein the image process comprises adjusting transparency of the 3-D model image.

8. A non-transient computer-readable storage medium having computer-implemented instructions stored thereon for providing an overlay image of an implant that, when executed by a mobile computing device storing a library of 3-D implant data including 3-D positions of radio-opaque internal markers in 3-D space, cause the mobile computing device to:
    receive an image of an imaging display device screen, the image including the implant and at least two of the radio-opaque internal markers being visible as fiducial markers within the image, the fiducial markers being 2-D positions of the radio-opaque internal markers in a 2-D plane;
    estimate a pose of the implant based on the relationship between the 2-D positions of the radio-opaque internal markers and the 3-D positions of the radio-opaque internal markers;
    retrieve or generate a 3-D model image of the implant at the determined pose using the 3-D implant data; and
    overlay the 3-D model image onto the captured image, wherein the 3-D model image is provided at the estimated pose over the implant.

9. The non-transient computer-readable storage medium of claim 8, wherein the estimated pose of the implant is defined by a projection transformation, and having further computer-implemented instructions stored thereon, that when executed by the mobile computing device, cause the mobile computing device to estimate a pose of the implant by deriving the projection transformation using the 2-D positions of the radio-opaque internal markers and the 3-D positions of the radio-opaque internal markers.

10. The non-transient computer-readable storage medium of claim 9, having further computer-implemented instructions stored thereon, that when executed by the mobile computing device, cause the mobile computing device to:
    receive information related to the implant and/or the surgical procedure; and
    use the received information when estimating the pose of the implant, wherein the received information is used to refine the derivation of the projection transformation.

11. The non-transient computer-readable storage medium of claim 10, wherein the information comprises at least one of an implant family, an implant size, an implant component, an imaging view and a surgical approach.

12. The non-transient computer-readable storage medium of claim 10, having further computer-implemented instructions stored thereon, that when executed by the mobile computing device, cause the mobile computing device to request information related to the implant and/or the surgical procedure under the condition that the pose of the implant cannot be derived.

13. The non-transient computer-readable storage medium of claim 8, having further computer-implemented instructions stored thereon, that when executed by the mobile computing device, cause the mobile computing device to perform an image process on the 3-D model image.

14. The non-transient computer-readable storage medium of claim 13, wherein the image process comprises adjusting transparency of the 3-D model image.

15. A mobile computing device for providing an overlay image of an implant, the implant including radio-opaque internal markers adjacent to and defining edges of the implant, comprising:
   a memory that stores a library of 3-D implant data including 3-D positions of the radio-opaque internal markers in 3-D space;
   an image capturing device configured to capture an image of an imaging display device screen, the image including the implant and at least two of the radio-opaque internal markers being visible as fiducial markers within the image, the fiducial markers being 2-D positions of the radio-opaque internal markers in a 2-D plane; and
   a processor configured to:
      estimate a pose of the implant based on the relationship between the 2-D positions of the radio-opaque internal markers and the 3-D positions of the radio-opaque internal markers;
      retrieve or generate a 3-D model image of the implant at the determined pose using the 3-D implant data; and
      overlay the 3-D model image onto the captured image, wherein the 3-D model image is provided at the estimated pose over the implant.

16. The mobile computing device of claim 15, wherein the estimated pose of the implant is defined by a projection transformation, and the processor is further configured to estimate a pose of the implant further by deriving the projection transformation using the 2-D positions of the radio-opaque internal markers and the 3-D positions of the radio-opaque internal markers.

17. The mobile computing device of claim 16, wherein the processor is further configured to:
   receive information related to the implant and/or the surgical procedure; and
   use the received information when estimating the pose of the implant, wherein the received information is used to refine the derivation of the projection transformation.

18. The mobile computing device of claim 17, wherein the information comprises at least one of an implant family, an implant size, an implant component, an imaging view and a surgical approach.

19. The mobile computing device of claim 16, wherein the processor is further configured to request information related to the implant and/or the surgical procedure under the condition that the pose of the implant cannot be derived.

20. The mobile computing device of claim 15, wherein the processor is further configured to adjust transparency of the 3-D model image.

* * * * *